(12) United States Patent
Silvester

(10) Patent No.: US 8,105,291 B2
(45) Date of Patent: Jan. 31, 2012

(54) DEVICE FOR STORING AND ADMINISTERING ACTIVE SUBSTANCES

(76) Inventor: Ivonne Silvester, Bingen (DE)

( * ) Notice: Subject to any disclaimer, the term of this patent is extended or adjusted under 35 U.S.C. 154(b) by 20 days.

(21) Appl. No.: 12/663,824

(22) PCT Filed: Jun. 5, 2008

(86) PCT No.: PCT/DE2008/000937
§ 371 (c)(1),
(2), (4) Date: Jan. 11, 2010

(87) PCT Pub. No.: WO2008/151606
PCT Pub. Date: Dec. 18, 2008

(65) Prior Publication Data
US 2010/0179474 A1  Jul. 15, 2010

(30) Foreign Application Priority Data
Jun. 9, 2007  (DE) .......................... 10 2007 026 752

(51) Int. Cl.
A61M 5/00 (2006.01)
(52) U.S. Cl. .............................. 604/191; 604/71; 604/72
(58) Field of Classification Search .................... 604/71, 604/72, 191
See application file for complete search history.

(56) References Cited

U.S. PATENT DOCUMENTS

| 3,714,943 A * | 2/1973 | Yanof et al. ..................... 604/70 |
| 4,327,724 A | 5/1982 | Birk et al. |
| 5,110,007 A * | 5/1992 | Law et al. ........................ 221/25 |
| 5,464,118 A * | 11/1995 | Grau et al. ......................... 221/5 |
| 5,865,796 A * | 2/1999 | McCabe ........................ 604/71 |
| 6,048,337 A * | 4/2000 | Svedman ...................... 604/313 |
| 6,789,497 B1 * | 9/2004 | Aiken ........................... 116/308 |
| 6,824,006 B2 * | 11/2004 | Lambelet, Jr. ................ 220/835 |
| 7,004,928 B2 * | 2/2006 | Aceti et al. .................... 604/191 |
| 7,503,324 B2 * | 3/2009 | Barney et al. ............ 128/203.21 |
| 7,582,063 B2 * | 9/2009 | Wurster et al. ................ 600/584 |
| 2004/0025871 A1 | 2/2004 | Davies |
| 2004/0134494 A1 | 7/2004 | Papania et al. |
| 2005/0074514 A1 * | 4/2005 | Anderson et al. ............. 425/461 |
| 2005/0106225 A1 * | 5/2005 | Massengale et al. .......... 424/448 |
| 2005/0133029 A1 * | 6/2005 | Nichols et al. ........... 128/203.26 |
| 2006/0157053 A1 * | 7/2006 | Barney et al. ............ 128/200.23 |
| 2007/0016163 A1 * | 1/2007 | Santini et al. ................. 604/500 |
| 2007/0151562 A1 * | 7/2007 | Jones et al. .............. 128/203.21 |
| 2009/0281657 A1 * | 11/2009 | Gak et al. ...................... 700/242 |

FOREIGN PATENT DOCUMENTS

| DE | 20218589 | 4/2003 |
| EP | 1757320 | 2/2007 |
| WO | WO96/11028 | 4/1996 |
| WO | WO 00/21587 | 4/2000 |
| WO | WO 02/074372 | 9/2002 |

* cited by examiner

Primary Examiner — Nicholas Lucchesi
Assistant Examiner — Diva Ranade
(74) Attorney, Agent, or Firm — Robert W. Becker; Robert Becker & Associates

(57) ABSTRACT

A device for storing and administering active substances, including a plurality of reservoirs for respectively accommodating at least one active substance. The reservoirs are disposed in a radial manner with an end face facing the direction of the center of the device. A mechanism is mounted in the device to open and close the reservoirs. A needle-free injection device delivers at least one active substance to a user.

11 Claims, 5 Drawing Sheets

DEVICE FOR STORING AND ADMINISTERING ACTIVE SUBSTANCES

BACKGROUND OF THE INVENTION

The instant application should be granted the priority dates of Jun. 9, 2007, the filing date of the corresponding German patent application 10 2007 026 752.7, as well as Jun. 5, 2008, the filing date of the International patent application PCT/DE2008/000937.

SUMMARY OF THE INVENTION

The invention relates to a device for storing and administering active substances.

As a health precaution, it is known to store active substances in a cooled manner in order to maintain their respective efficacy even over a long period of time. For this purpose, it is customarily necessary to store these active substances in a refrigerator. Active substances must generally be taken at periodically determined intervals, or, for example with diabetics, as a function of blood sugar level, that, among other reasons, varies due to the consumption of food. For this purpose, such a patient can carry a so-called "diabetic clock".

Furthermore, merely one reservoir with one active substance is present, for which reason the supply or delivery of a number of active substances can be guaranteed only by the use of a number of appropriate devices.

It is an object of the invention to provide a device for storing and administering a plurality of active substances that is easy to handle and that enables a user to move independently and freely.

Pursuant to the invention, the object is realized in that the device includes a plurality of reservoirs for respectively accommodating at least one active substance, and a needle-free injection device for the supply or delivery of one or more active substances to a user.

An important concept of the invention is that the device is embodied with a reservoir for any number of desired active substances in a form, size and weight that corresponds to that of a conventional wrist watch. Thus, the reservoirs or supply containers with the active substances, such as, for example, enzymes, propolis, acids, bases, vitamins, minerals, vital substances, and the like, can always comfortably be carried by a user. By means of the needle-free injection device, an active substance stored in the reservoir can be administered to the user, whereby it is to be understood that also a combination of active substances from different reservoirs can be dispensed. The device can, of course, be provided with an aesthetically pleasing design.

So that when a plurality of reservoirs are accommodated the device has a compact configuration, the reservoirs are preferably disposed in a radial or star-shaped manner with an end face facing in the direction of the center, and a mechanism for opening and closing the reservoir, in particular a computer-controlled mechanism, is mounted in the device and is preferably rotatable by means of a motor. By means of the mechanism for opening and closing the reservoirs, which is in particular driven by a motor, the quantity of the active substance delivered from the respective reservoir can be determined relatively exactly.

The configuration of the mechanism includes two concentrically mounted rings that each has an opening and that can be rotated not only relative to one another but also relative to the reservoirs, whereby the opening of the inner ring is coupled with the needle-free injection device. To deliver a specific active substance, the opening of the outer ring rotates to the appropriate reservoir, and after an appropriate rotational movement, for example for a certain time period, the inner ring releases the opening of the outer ring, whereupon the appropriate active substance passes to the needle-free injection device. This process of removing the active substance can be repeated at various reservoirs in order to assemble the desired active substance combination. The needle-free injection device serves for the administration or supply of the active substances to a user. A number of needle-free injection devices are known to one of skill in the art. These injection devices transport, for example, liquid active substances through the skin of the user utilizing spring force which generates a high pressure.

Pursuant to a further development, each reservoir is comprised of a flexible material, in particular silicone rubber, and each individual reservoir is supplied with pressure separately, or all reservoirs are supplied in common with pressure. To supply pressure to the reservoir, a flexible thrust ring is expediently disposed in the device and actuates the reservoir with a force to increase the internal pressure. The thrust ring can, for example, be filled with air, or due to its elastic material characteristics can compress the relatively soft reservoirs.

So that a defined quantity of active substance is delivered from the reservoir, a pressure or position sensor that is connected with a computer control is preferably associated with at least one reservoir and/or the thrust ring, whereby the computer control includes at least one storage module and/or an interface, and is connected with an input and/or output device that preferably includes at least one contact switch and at least one control light. By means of the contact switch or the interface, data relative to the active substances present in the reservoirs, the quantity thereof that is to be administered, as well as the time at which the active substances are to be delivered, can be input and can be stored in the storage module, in particular in an over-writable manner. It is, of course, possible for the computer to control the mechanism for the opening and closing of the reservoirs and/or for the needle-free injection device. For inputs directly to the device, the at least one contact switch or key is available. The output device, which, for example, is realized as a multi-color LED or an audio-response unit, informs the user of the device, for example concerning the filling level of the reservoirs. In addition to an individual compilation of active substances that are to be delivered, further data pertinent to the user can be stored on the storage module in a secured manner; such data, in addition to name, age, address and sex, can, for example, include information regarding body mass index, hobbies, calorie consumption, state of health, medications taken, and the like. Due to the computer control of the device, it is, for example, possible by means of a litmus strip to determine a pH value of the saliva of the user, and to input this into the device, which as a consequence releases appropriate active substances. Similarly, active substances can be released in a periodically desired sequence. Furthermore, it is possible for the device to detect and monitor further biometric data of the user, for example pulse, skin temperature and the like, by means of suitable sensors.

Pursuant to a further embodiment, the reservoirs can be replaced individually or in common, or can be provided with a unit for filling with any desired active substances, whereby the unit for the filling includes a capillary tube that proceeds from the opening of the inner ring and extends in the direction of the center of the ring, and that preferably at the end includes a telescopable pin, in particular of silicone rubber, having at least one opening through which an active substance can pass. The pin of the unit for the filling can be extended in order to convey the active substance out of the supply container through pores or openings and into the appropriate reservoir. If the reservoirs of the device, as described subsequently, are preferably filled at a filling station, the unit for the filling is of course connected with the computer. To begin the filling or refilling, the mechanism for the opening and closing of the reservoirs is moved into a specific position, and information relative to the active substances contained in the device or the position of the reservoir is exchanged to ensure that the reservoirs present in the device are also filled with appropriate active substance. The correct position of the telescopic pin and/or of the mechanism for the opening and closing and/or the level of filling of the reservoir are monitored by sensors.

The capillary tube is expediently connected to the needle-free injection device, and not only the device for the supply of the active substance, or a combination of active substances from several reservoirs, to a user, but also the unit for the filling of the reservoirs, are covered by a displaceable orifice plate when not in use. The orifice plate can, for example, be automatically opened when the device is turned on or off, or during actuation of the device for the supply of the active substance or of the unit for the filling of the reservoirs. It is to be understood that all components of the device are disposed in a housing, in order in particular to protect the reservoirs from external influences.

Preferably, a delivery of the active substances can in particular be prescribed in a personalized manner. To prevent misuse of the device, it can be personalized. For this purpose, among others, a fingerprint sensor, an iris scanner, or the like can be provided in order to determine the identity of the user and his or her authorization. In the same manner, a code word, a PIN or the like can be input, or the device can be provided with speech and voice recognition in order to deliver an active substance only to an authorized user. In this connection, the device can also be embodied in such a way that release, in particular to children or infirm people, is effected by an authorized person.

The form, size and weight of the device preferably conforms to that of a wrist watch; a refrigerant storage means, in particular for liquid helium, and possibly solar cells, for the supply of energy, are provided, whereby the device is, for example, provided with a dirt-repelling surface, in particular in conformity with the lotus effect. By means of the refrigerant storage means, which can have any desired configuration, the active substances are cooled and their efficacy is maintained. The refrigerant storage means is expediently in the form of a container for liquid helium in order to obtain a maximum cooling capacity. In this connection, a spatial gap, for example 0.5 mm, can be selected between a surrounding housing of the device and the actual refrigerant storage means in order to obtain a comfortable carrying feeling of the wristband-like device. The refrigerant storage means preferably encases or envelops the reservoirs on all sides in the form of a vacuum bottle for liquid helium in order to cool the reservoirs. Present at the refrigerant storage means is not only a filler connection for the liquid helium, but also an overflow valve in order to be able to draw off vaporized helium. For the supply of energy the device can be provided with a battery or a storage cell; however, it is preferably equipped with solar cells for the generation of the required electrical current. Coatings on surfaces for achieving the lotus effect are known in the state of the art.

To use the device, it is turned on by pressing an ON button or key, and by means of the interface there is effected an adjustment between data of the device and data of a central computer, which is integrated for example in a home filling station, for the actual vital material daily requirement determination of the user of the device, who is in particular to be identified by a speech/voice recognition program. Effected at specific time intervals is the calculation of the energy conversion of the user on the basis of a basal metabolism, i.e. the calorie consumption for bodily functions. The cholesterol/calcium/vitamin D management is controlled for older users. A red luminous signal of the output device, which is embodied in the manner of a traffic light, provides, for example, an indication that too little or too much liquid was supplied, or whether the daily requirement of certain substances is not adequately covered or is covered in excess. The device releases active substances in a computer-controlled manner in order to eliminate corresponding deficits. Furthermore, by means of an appropriate output device behavior or condition-related suggestions can be provided, for example indications of foods and/or herbs that are to be avoided. With a green luminous signal, no action of the device is effected, since no alarming data is present. To aid in recovery, the device releases the suitable active substances in suitable quantities in a specific sequence, and provides information regarding suitable medicinal herbs. As soon as the device is removed or taken off, for example when going to sleep, it is deactivated by opening a clasp of the arm band.

In order, for example when traveling, to again refill the device, pursuant to a further development a system is provided that on the one hand includes a previously described device, and on the other hand includes a filling station. Such a filling station, with appropriately sized supply containers for various active substances, can be embodied so as to be not only publicly accessible but also as a private filling station. Provided in the filling station are various reservoirs for various active substances, which in particular are all made of silicone rubber and are also cooled, and which, for example, are regularly refilled with active substances by a user or manager. It is to be understood that for this purpose the active substances must respectively be packaged so as to be suitably air tight and/or light proof. The refilling of a private filling station is effected by the user himself or herself, who for this purpose purchases appropriate reservoirs of the respectively desired active substances, and can thus refill his or her filling station. Associated with the reservoirs of the filling station is the mechanism for the delivery of active substances to the device; this mechanism in particular includes two concentrically mounted rings, each of which has an opening and which are rotatable not only relative to one another but also relative to the reservoirs, whereby the inner ring communicates with a line for coupling, with the device. The line is provided with a closable outlet for connection to the unit for the filling of the device, in particular to the telescopable pin thereof.

For the filling or refilling, the wristwatch-like device is placed in a suitable holder on the filling station, and the closable outlet of the filling station is coupled to the telescope-like pin of the device, so that the reservoir in the device can be filled. An appropriate payment can be effected in a manner other than with cash, or by depositing coins or bank notes.

Since the device is to be filled individually, in particular with a public filling station a personalization is advantageous in order to prevent an incorrect filling of the reservoirs in the device. The filling station is preferably computer controlled, and communicates via an interface with the device or with a central computer. Consequently, the filling station can determine with which active substances and in which combination the device is to be filled.

To ensure that the device, i.e. its reservoir, is filled with the individually determined mixture of active substances, the filling station expediently includes a discharge mechanism for the device. Prior to each filling, the device is first completely emptied by means of the discharge mechanism. The discharge mechanism can, for example, contain a disposal container for the active substances of the device. Furthermore, in addition or as an alternative, a cleaning device for the device and/or the mechanism for the dispersal of active substances to the device can be provided.

The filling station preferably has an input and/or output device that is connected to the computer. With the private filling station, for example a green luminous signal indicates that the device is loaded or charged.

It is to be understood that the previously mentioned and yet to be explained features can be used not only in the respectively indicated combination, but also in other combinations. In the scope of the invention is defined only by the claims.

BRIEF DESCRIPTION OF THE DRAWINGS

The invention will be explained in greater detail subsequently with the aid of an exemplary embodiment and with reference to the drawings, in which.

DESCRIPTION OF SPECIFIC EMBODIMENTS

Figure 1:
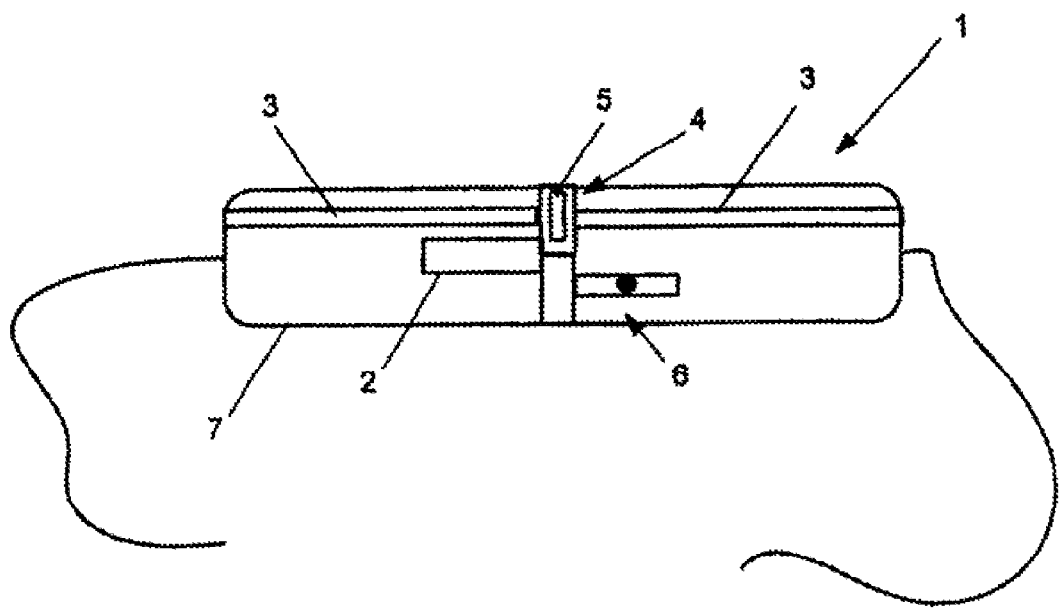
FIG. 1 is a schematic illustration of an exemplary inventive device.
Figure 2:
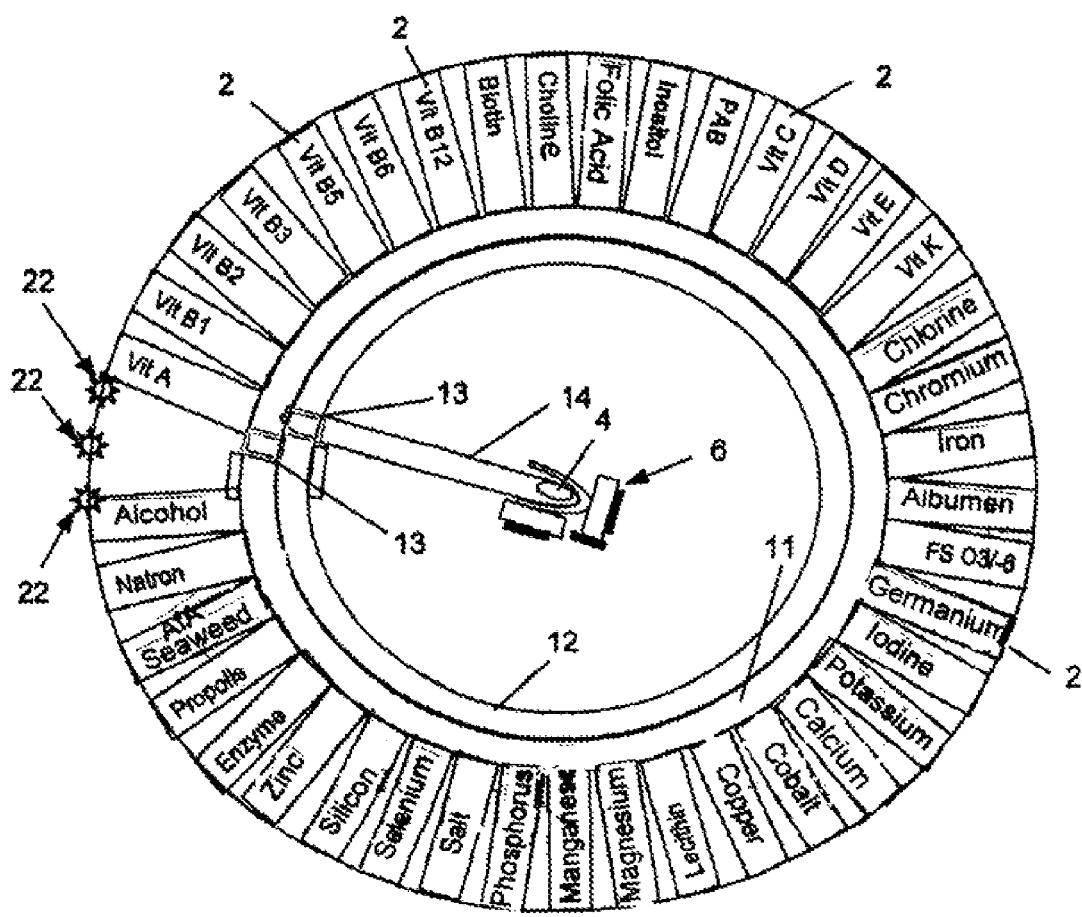
FIGS. 2-5 are schematic cross-sectional illustrations through the device of FIG. 1 in various operating states.
Figure 3:
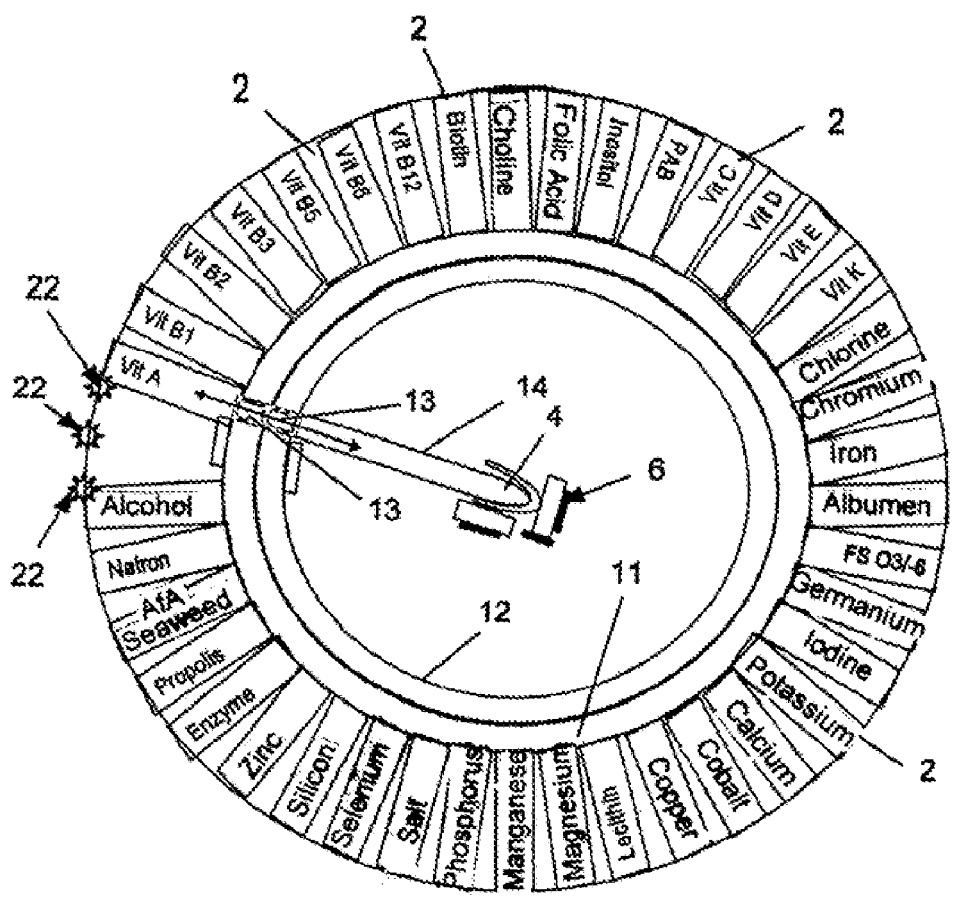
Figure 4:
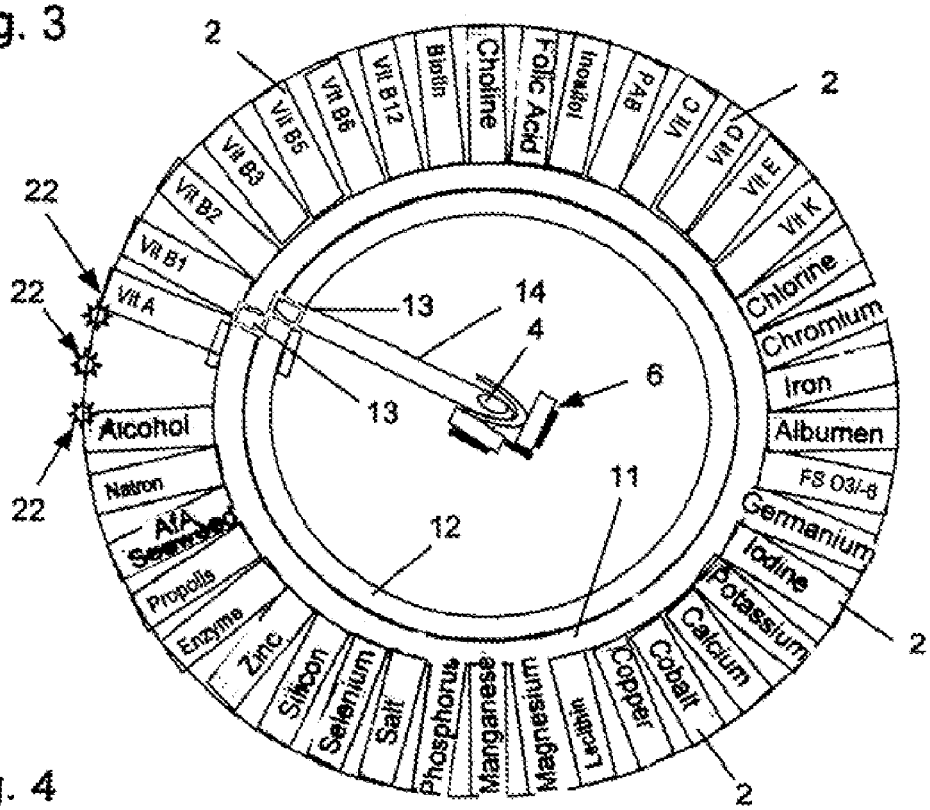
Figure 5:
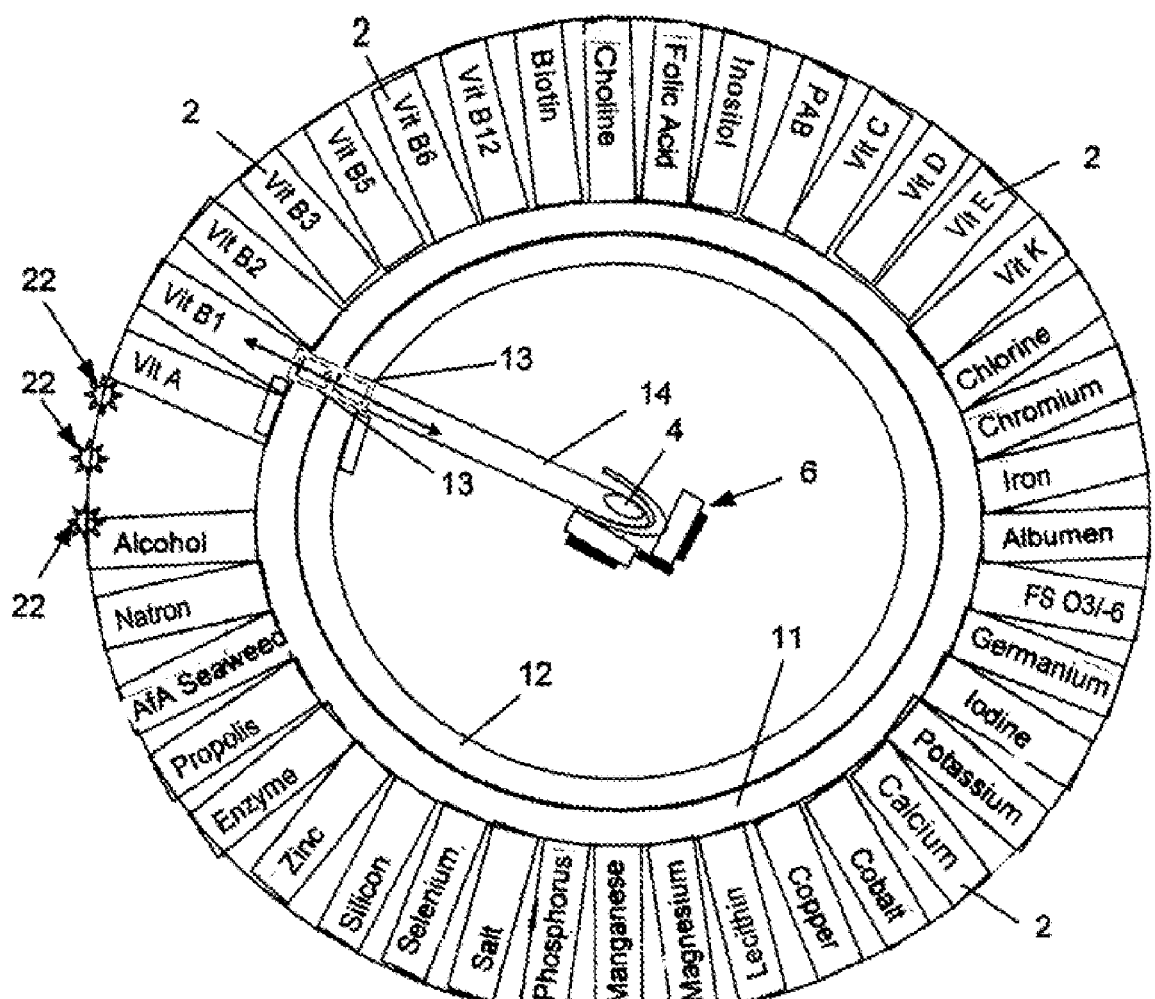
Figure 6:
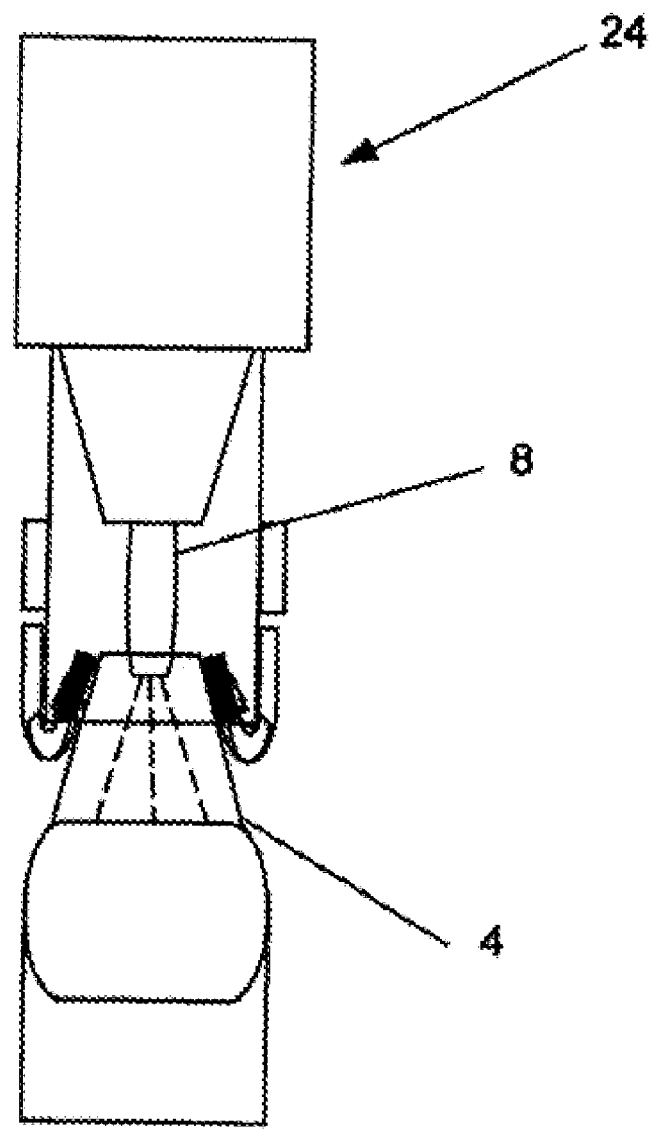
FIG. 6 is a schematic partial illustration of a system that includes the device of FIG. 1 and a filling station.
Figure 7:
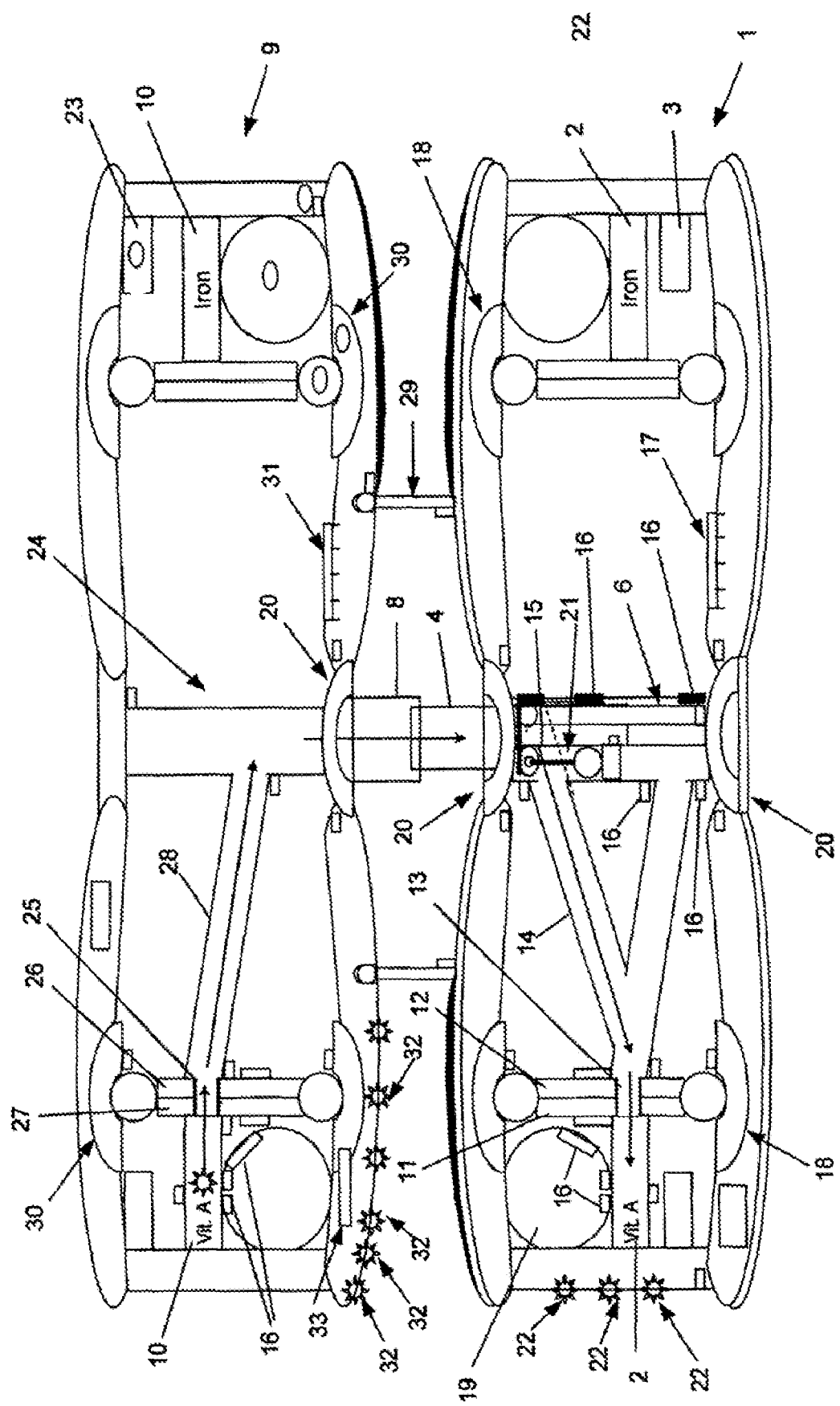
FIG. 7 is a schematic cross-sectional illustration through the system of FIG. 6.

The device 1 for the storing and administration of active substances is provided with a plurality of reservoirs 2 of silicone rubber, in which any desired active substances, such as enzymes, propolis or the like, pure food stuffs, medicines or drugs are stored. In order to permanently maintain the efficacy of the active substances, a refrigerant storage means 3, in particular in the form of a vacuum bottle or cylinder for helium, is associated with the device 1. A telescopable pin 4 serves for the filling or refilling of the reservoir 2; the pin can be extended and retracted under air pressure, the effect of vacuum, or mechanical action, whereby the pin 4 can be made of silicone rubber and has an opening 5 for the active substance. If the extended pin 4 rests against a corresponding, for example telescopable, outlet 8 of a public or private filling station 9, the active substances, from a reservoir 10 of a filing station 9 which in particular with respect to the arrangement of the reservoir 10 can be embodied in further parts in correspondence with the device 1, can thus pass into the reservoir 2 of the device 1 in order to again fill the latter. For this purpose, a device 1 is in particular personalized in order to prevent misuse of the device 1.

For the release of active substances to a user, a device for the supply of the active substance to a user is embodied as a needle-free injection device 6, which includes a spring mechanism in order to convey active substance out of the reservoir 2 by means of high pressure through the skin of the user, where the active substance can deploy its effect.

The device 1 is provided with an attractive housing 7 of the type of a wrist watch having a pertaining wrist band in order to obtain an aesthetic outward appearance.

The reservoirs 2 are arranged in a radial or star-shaped manner, with one end face facing the direction of the center of the device 1; a computer-controlled mechanism for the opening and closing of the reservoirs 2, in the form of two rings 11, 12 that are rotatable by motors and that are each provided with an opening 13, is mounted in the device 1. The concentrically mounted rings 11, 12 are rotatable not only relative to one another but also relative to the reservoirs 2 in appropriate bearings 18, whereby the opening 13 of the inner ring 12 is on the one hand coupled with the needle-free injection device 6, and on the other hand is coupled with a capillary tube 14 that extends in the direction of the center of the ring 12 and that at its end carries the telescopable pin 4. A channel 15 for the flow or passage of active substances in the direction of the needle-free injection device 6 or of the pin 4 is provided with a valve mechanism 21. The position of the rings 11, 12 as well as of the pin 6, the needle-free injection device 4, the pressure in the channel 15, the pressure in the reservoirs 2, and the level of filling as well as the temperature in the reservoirs 2 are monitored by sensors 16, which are connected with a computer control 17. For the application of pressure to the reservoirs 2, a flexible thrust ring 19 is disposed in the device 1. The openings for the injection device 6 and the pin 4, which can of course also be disposed on a side of the device, are closed-off by means of an orifice plate 20. The computer control 17 is connected with input and output devices 22.

Furthermore, an interface 29 for the mechanical and/or electrical coupling of the device 1 with the filling station 9 is provided that also has the radially disposed flexible reservoirs 10 of a refrigerant storage means 23 and in addition has a device 24 for releasing active substances to the device 1. The device 24 for releasing active substances to the device 1 includes two concentrically mounted rings 26, 27 that each have an opening 25 and that can be rotated by motors not only relative to one another but also relative to the reservoirs 10, whereby the inner ring 26 communicates with a line 28 for coupling with the device 1 via the outlet 8, and the rings 26, 27 are held in the filling station 9 by means of bearings 30. The filling station 9 includes a computer 31, to which are connected input/output devices 32 and sensors 16, whereby the input/output devices 32, which include, for example, colored LEDs, also serve for the representation of the states of the filling station 9 or the level of filling of the reservoirs 10.

If there is no active substance in at least one reservoir 2 of the device 1, this is made recognizable to the user by a red illumination of one of the LEDs of the input/output device 22, and at the same time the device 1 is made inoperable since a reliable supply of active substances to the user cannot be guaranteed. The user subsequently connects the device 1 to the filling station 9, and either automatically or after activation of one or more contact switches of the input/output devices 32, 22 of the filling station 9 or device 1 respectively, a data transfer begins relative to the active substances present in the device 1 and possibly to be refilled. This also ensures that the openings 13 of the rings 11, 12 of the device 1, and the openings 25 of the rings 26, 27 of the filling station 9, are in a starting position, and after the opening of the orifice plate 20 that is associated with the outlet 8, the outlet 8 moves out of the filling station 9 in order to contact the pin 4 of the device 1, which also after the opening of the associated orifice plate 20 telescopes, so that active substance can flow out of the filling station 9 into the appropriate reservoir 2 of the device 1. For this purpose, the openings 13 of the rings 11, 12 of the device 1 are rotated in a computer-controlled manner in front of the reservoir 2 that is to be filled, and the openings 25 of the rings 26, 27 are rotated in front of the appropriate reservoir 10 of the filling station 9. The level of filling of the reservoirs 2, 10 is monitored by the associated sensor 16, in a computer-aided manner. After the conclusion of the filling or refilling process, during which possibly several reservoirs 2, 10 are successively moved into place, the filling station 9 and the device 1 return to their respective starting states, in which the orifice plates 20 are closed.

The assembly and delivery of active substances is effected in a computer-controlled manner on the basis of stored starting data. After the active substances that are to be delivered are present in the needle-free injection device 6, into which they have been metered by the opening and closing of the openings 13, they can be released automatically or by the activation of a key of the input and output device 22.

Personalization or customization of the device 1 and of the filling station 9 is effected, for example, by means of the respective input/output device 22, 32. By means of a payment device 33, it is possible to make payment at a publically accessible filling station 9.

The specification incorporates by reference the disclosure of German 10 2007 026 752.7 filed Jun. 9, 2007, as well as International application PCT/DE2008/000937, filed 5 Jun. 2008.

The present invention is, of course, in no way restricted to the specific disclosure of the specification and drawings, but also encompasses any modifications within the scope of the appended claims.

REFERENCE NUMERAL LIST

1. Device
2. Reservoir
3. Refrigerant Storage Means
4. Pin
5. Opening
6. Injection Device
7. Housing
8. Outlet of 9
9. Filling Station
10. Reservoir of 9
11. Ring of 1
12. Ring of 1
13. Opening
14. Capillary Tube
15. Channel
16. Sensor
17. Computer Control
18. Bearings
19. Thrust Ring
20. Orifice Plate
21. Valve Mechanism
22. Input/Output Devices
23. Refrigerant Storage Means of 9
24. Device
25. Opening
26. Ring
27. Ring
28. Line
29. Interface
30. Bearings
31. Computer
32. Input/Output Devices
33. Payment Device

The invention claimed is:

1. A device for storing and administering active substances, comprising:
   a plurality of reservoirs for respectively accommodating at least one active substance, wherein said reservoirs are disposed in a radial manner with an end face facing in the direction of a center of said device, wherein each of said reservoirs is made of a flexible material, and wherein either each individual reservoir is adapted to be acted upon by pressure, or all of said reservoirs are adapted to be acted upon by pressure in common;
   a mechanism mounted in said device and configured to open and close said reservoirs, wherein said mechanism includes two concentrically mounted rings that are each provided with an opening, wherein said rings are rotatable not only relative to one another but also relative to said reservoirs, and wherein said opening of an inner one of said rings is coupled to said needle-free injection device;
   a flexible thrust ring disposed in said device for pressurization of said reservoirs, wherein said thrust ring actuates said reservoirs with a force for increasing an internal pressure thereof; and
   a needle-free injection device configured to deliver at least one active substance to a user.

2. A device according to claim 1, wherein said mechanism is computer controlled.

3. A device according to claim 2, wherein said mechanism is configured to be rotated by motor.

4. A device according to claim 1, which includes a pressure or position sensor that is connected with a computer control, wherein said pressure or position sensor is associated with at least one of the group consisting of at least one of said reservoirs and said thrust ring, further wherein an input and/or output device is provided, and wherein said computer control includes a storage module and/or an interface, and is connected to said input and/or output device.

5. A device according to claim 4, wherein said input and/or output device includes at least one contact switch and at least one control light.

6. A device according to claim 1, wherein said reservoirs are configured to be exchanged individually or in common, or are provided with a unit for filling said reservoirs with active substances, further wherein said unit for filling said reservoirs includes a capillary tube that proceeds from said opening of said inner ring and extends in the direction of the center of said ring, and wherein said capillary tube includes a telescopable pin having at least one opening for the passage of an active substance therethrough.

7. A device according to claim 6, wherein said telescopable pin is made of silicone rubber and is disposed on an end of said capillary tube.

8. A device according to claim 6, wherein said capillary tube is connected with said needle-free injection device, and wherein an orifice plate is provided for covering not only a mechanism for supplying an active substance, or a combination of active substances from a plurality of said reservoirs, to a user, but also said unit for filling said reservoirs, when said device is not in use.

9. A device according to claim 1, which is configured to deliver active substances in a manner customized to a particular user.

10. A device according to claim 1, which is configured in form, size and weight in conformity with a wristwatch, wherein a refrigerant storage means is provided, and wherein said device has a dirt-repelling surface in conformity with the lotus effect.

11. A device according to claim 10, wherein solar cells are provided for the supply of energy.

\* \* \* \* \*